Figure 1:
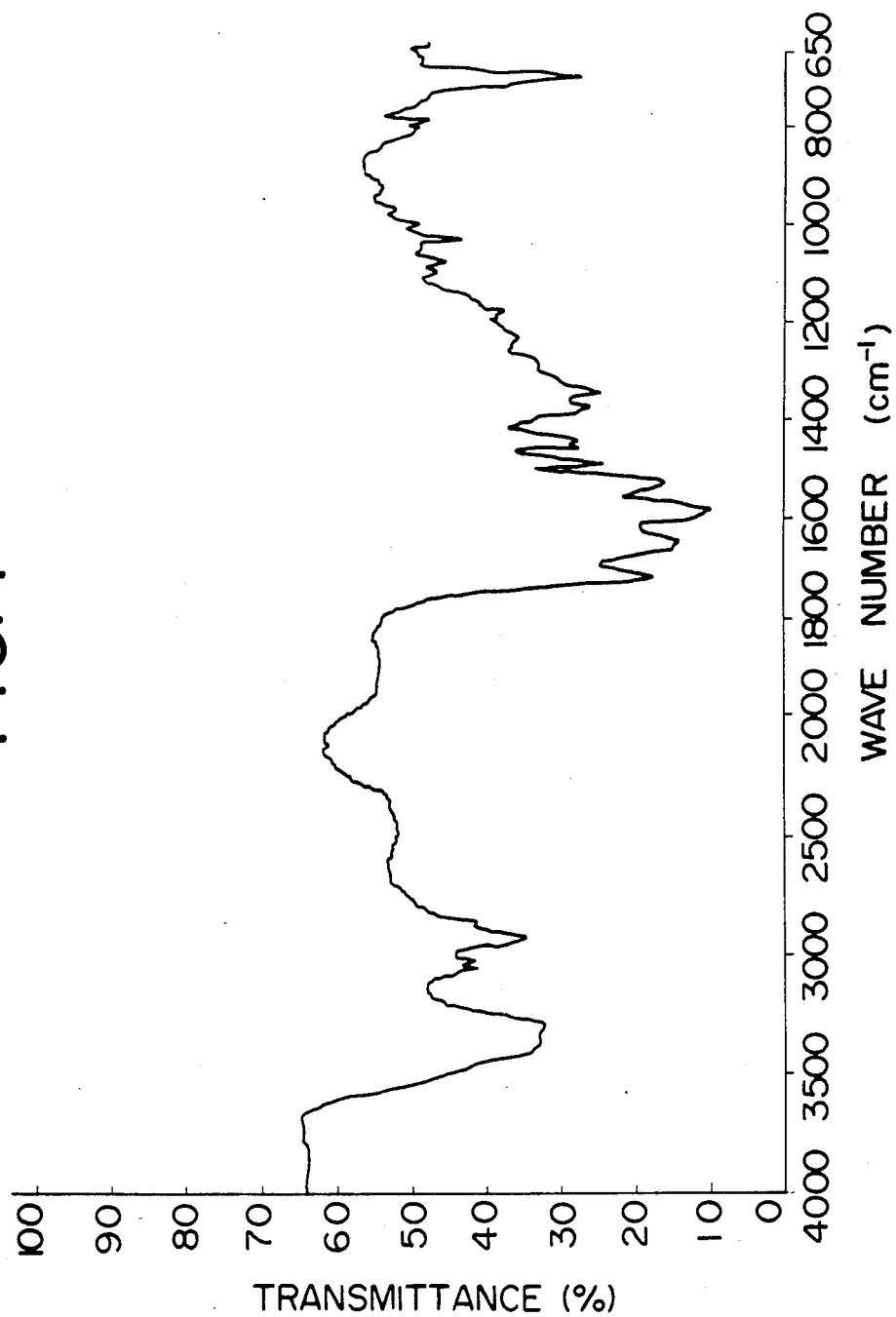

United States Patent [19]

Umezawa et al.

[11] Patent Number: 4,661,495
[45] Date of Patent: Apr. 28, 1987

[54] ARPHAMENINE-RELATED COMPOUNDS USEFUL FOR POTENTIATING THE IMMUNE RESPONSE IN A LIVING ANIMAL

[75] Inventors: Hamao Umezawa; Tomio Takeuchi, both of Tokyo; Takaaki Aoyagi, Fujisawa; Shokichi Ohuchi, Kawasaki, all of Japan

[73] Assignee: Zaidan Hojin Biseibutsu Kagaku Kenkyu Kai, Tokyo, Japan

[21] Appl. No.: 769,076

[22] Filed: Aug. 26, 1985

[30] Foreign Application Priority Data

Sep. 3, 1984 [JP] Japan .................................. 59-182788

[51] Int. Cl.$^4$ .................... A61K 31/495; C07D 239/02
[52] U.S. Cl. ...................................... 514/275; 544/332
[58] Field of Search .......................... 544/332; 574/275

[56] References Cited

FOREIGN PATENT DOCUMENTS 96356 12/1983 European Pat. Off. .
212791 12/1983 Japan .

OTHER PUBLICATIONS

Ohuchi et al., J. of Antibiot. 1984, 37(12) 1741–3.
Ohuchi et al, J. of Antibiot. 1983, 36(11) 1576–80.
Ohuchi et al, Chem. Abst. 100-175223k.
Ohuchi et al, Chem. Abst. 100-101620r.
Ohuchi et al, Chem. Abst. 102-74753u.

Primary Examiner—Donald G. Daus
Assistant Examiner—Cecilia Shen
Attorney, Agent, or Firm—Larson and Taylor

[57] ABSTRACT

New arphamenine-related compounds are now provided, which are represented by the formula

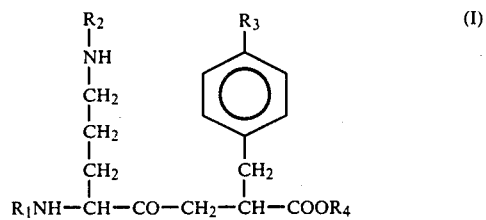

wherein $R_1$ denotes a hydrogen atom or an amino-protecting group, $R_2$ denotes a dimethylpyrimidinyl group, $R_3$ denotes a hydrogen atom or a hydroxyl group, and $R_4$ denotes a hydrogen atom or a carboxyl-protecting group. The new arphamenine-related compounds exhibit a carboxypeptidase-inhibitory activity and also an immunopotentiating activity and are useful for potentiating the immune response in a living animal.

5 Claims, 4 Drawing Figures

ARPHAMENINE-RELATED COMPOUNDS USEFUL FOR POTENTIATING THE IMMUNE RESPONSE IN A LIVING ANIMAL

SUMMARY OF THE INVENTION

This invention relates to new arphamenine-related compounds and pharmaceutically acceptable salts and ester thereof which exhibit an immunopotentiating activity. This invention also relates to a pharmaceutical composition useful as immunopotentiator which comprises the new arphamenine-related compound as the active ingredient, and this invention further relates to a method for potentiating or stimulating the immune response in a living animal.

BACKGROUND OF THE INVENTION

In these years, we, the present inventors, have paid attention on that some chemical compounds having an aminopeptidase-inhibitory activity exhibit an immunopotentiating activity and an antitumor activity. Recently we have discovered arphamenines A and B and we have found that these arphamenines and some arphamenine-related compounds exhibit physiological activities, including the immunopotentiating activity and the antitumor activity (see Japanese patent application first publication "Kokai" No. 212791/83; pending U.S. patent application Ser. No. 500,396; pending U.S. patent application Ser. No. 619,322 and EPC patent application No. 83105416.8, for example).

Chemical structure of the arphamenine is represented by the following general formula:

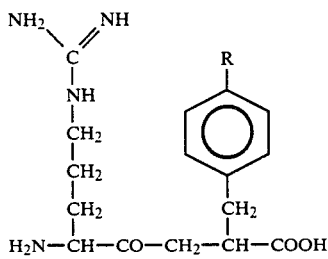

wherein R is a hydrogen atom or a hydroxyl group. Herein, "arphamenine" is a generic name of arphamenines A and B. The compound of the formula above where R is a hydrogen atom denotes arphamenine A, and the compound of the formula above where R is a hydroxyl group denotes arphamenine B.

On the other hand, we have found that benzylmalic acid having a carboxypeptidase-inhibitory activity shows an immunopotentiating activity ("J. Antibiot.", 37, 682 (1984)).

On the basis of these findings, we have now synthesized a further class of new arphamenine-related compounds represented by the following general formula (I)

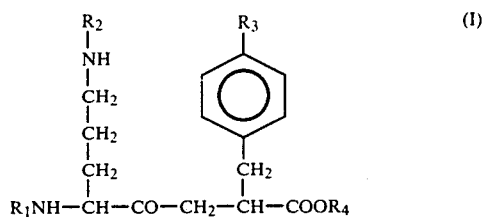

wherein $R_1$ denotes a hydrogen atom or an amino-protecting group, $R_2$ denotes a dimethylpyrimidinyl group, $R_3$ denotes a hydrogen atom or a hydroxyl group, and $R_4$ denotes a hydrogen atom or a carboxyl-protecting group. We have now examined these new arphamenine-related compounds for their physiological activities. As a result, it has been confirmed that these new compounds exhibit a carboxypeptidase-inhibitory activity and an immunopotentiating activity. Thus, we have accomplished this invention.

According to a first aspect of this invention, therefore, there is provided as the new compound an arphamenine-related compound represented by the formula (I)

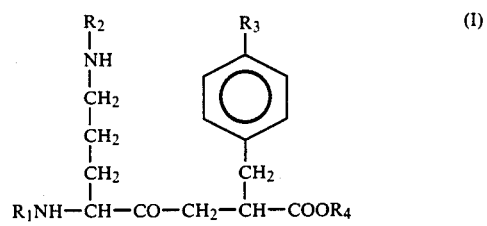

wherein $R_1$ denotes a hydrogen atom or an amino-protecting group, $R_2$ denotes a dimethylpyrimidinyl group, $R_3$ denotes a hydrogen atom or a hydroxyl group, and $R_4$ denotes a hydrogen atom or a carboxyl-protecting group, or a pharmaceutically acceptable salt or ester thereof.

In the formula (I) above, $R_1$ denotes a hydrogen atom or an amino-protecting group. This amino-protecting group may be an alkoxycarbonyl group such as t-butoxycarbonyl group (usually abbreviated as Boc), an aralkoxycarbonyl group such as benzyloxycarbonyl group (abbreviated as Z) and p-methoxybenzyloxycarbonyl group (abbreviated as Z(OMe)), and an acyl group, including an aliphatic acid residue, for example, an alkanoyl group such as acetyl group, propionyl group and palmityl group etc., and an aroyl group such as benzoyl group.

In the formula (I) above, $R_2$ denotes such a dimethylpyrimidinyl group as derived from the guanidyl group of arphamenine, especially 4,6-dimethylpyrimidin-2-yl group.

Further, in the formula (I), $R_4$ denotes a hydrogen atom or a carboxyl-protecting group. The carboxyl-protecting group includes an alkyl group such as methyl group, ethyl group, propyl group and t-butyl group etc.; and an aralkyl group such as benzyl group, p-nitrobenzyl group and p-methoxybenzyl group, and the like.

According to a preferred embodiment of the first aspect invention, there is provided a compound of the formula (I) where $R_1$ is a hydrogen atom, a benzoyl group or a benzyloxycarbonyl group, $R_2$ is a 4,6-dimethylpyridine-2-yl group, $R_3$ is a hydrogen atom or a hydroxyl group, and $R_4$ is a hydrogen atom.

Particular examples of the compound of the formula (I) are listed below:

Compound No. 1: 5-Benzoylamino-8-[(4,6-dimethylpyrimidin-2-yl)amino]-2-phenylmethyl-4-oxo-octanoic acid.

Compound No. 2: 5-Benzoylamino-8-[(4,6-dimethylpyrimidin-2-yl)amino]-2-(4'-hydroxyphenylmethyl)-4-oxo-octanoic acid.

Compound No. 3: 5-Benzyloxycarbonylamino-8-[(4,6-dimethylpyrimidin-2-yl)amino]-2-phenylmethyl-4-oxo-octanoic acid.

Compound No. 4: 5-Benzyloxycarbonylamino-8-[(4,6-dimethylpyrimidin-2-yl)amino]-2-(4'-hydroxyphenylmethyl)-4-oxo-octanoic acid.

Referring to the attached drawings:

FIG. 1, FIG. 2, FIG. 3 and FIG. 4 show the infrared absorption spectra of the above-identified Compounds Nos. 1 to 4 of this invention as produced in Example 1(b), Example 2(b), Example 3(b) and example 4(b) given herein after, respectively.

Examples of the medicinally acceptable or pharmaceutically acceptable salt of the compound of the formula (I) include such salts of the carboxyl group existing in said compound with a pharmaceutically acceptable cation, for example, cations of an alkali metal such as sodium and potassium etc.; and an alkaline earth metal such as calcium and magnesium etc., and ammonium ion. Examples of the salts of the compound of the general formula (I) also include such salts of the dimethylpyrimidinyl group and the amino group existing in said compound with a pharmaceutically acceptable inorganic acid or organic acid such as hydrochloric acid, hydrobromic acid, sulfuric acid, phosphoric acid, methanesulfonic acid, acetic acid, propionic acid, fumaric acid, maleic acid, malonic acid, benzoic acid, salicylic acid, phenylacetic acid and benzenesulfonic acid, and the like.

The pharmaceutically acceptable ester of the compound of the formula (I) may be an ester of the carboxyl group of said compound with an alkyl group of 1 to 4 carbon atoms such as methyl, ethyl and propyl; an alkoxyalkyl group such as ethoxyethyl; and pivaloyloxymethyl group, for example. The production and uses of these salts and esters are therefore also within the scope of this invention.

The arphamenine-related compound (I) according to this invention may be produced by chemical modification of the amino group and the guanidyl group and/or salt-forming reaction of the carboxyl group of arphamenine in a known manner. Thus, when the introduction of an amino-protecting acyl group into the amino group of arphamenine for the chemical modification of said amino group is to be conducted by benzoylation or generally by acylation, arphamenine may be reacted with benzoyl chloride or generally with an acylation reagent in an aqueous solution of sodium carbonate. After the reaction is completed, ethyl ether is added to the reaction solution to precipitate the N-benzoyl-arphamenine or generally an N-acyl-arphamenine. When the chemical modification of the guanidyl group of arphamenine by dimethylpyrimidylation is effected, an N-protected arphamenine may be reacted with 2,4-pentanedione in a mixture of potassium carbonate-dioxane-water at 37° C. After the reaction is finished, the reaction mixture is adjusted to pH 5.0 to precipitate the N-protected-dimethylpyrimidylated arphamenine. Furthermore, when the chemical modification of the carboxyl group of arphamenine is to be effected by esterification, for example, by esterification with n-propyl, arphamenine may be kept in n-propyl alcohol containing boron trifluoride (BF$_3$) overnight, followed by concentrating the reaction mixture and passing the concentrated solution through a column of Sephadex LH-20, so that the arphamenine n-propyl ester is afforded. The removal of the amino-protecting groups and the carboxyl-protecting groups may be achieved in a conventional manner.

The physiological activities of the compounds according to this invention are described below.

(1) Method of testing the inhibitory activity of the compounds to carboxypeptidase A:

The carboxypeptidase A-inhibitory activity was determined according to a modification of the method of Hayakari et al. (M. Hayakari et al., "Analytical Biochemistry" 84, 361–369, 1978). Thus, a mixture of 0.05 ml of a solution of 10 mM hippuryl-L-phenylalanine (as substrate), 0.25 ml of 0.05 M Tris-hydrochloride buffer (pH 7.5) containing 0.9 M NaCl and 0.15 ml of a solution containing a test compound as produced in Example 1, 2, 3 or 4 shown hereinafter was heated at 37° C. for 3 minutes. To said mixture was then added 0.05 ml of a carboxypeptidase A (Type 1, as extracted from bovine pancreas, a product of Sigma Co.), and the enzymatic reaction was effected at 37° C. for 30 minutes. The reaction solution was admixed with 0.03 ml of aqueous 1N sodium hydroxide to stop the reaction. After allowing to stand at ambient temperature for 15 minutes, the reaction solution was admixed with 2 ml of 0.06 M phosphate buffer (pH 7.2) and with 2 ml of a solution of 1% cyanuric chloride in ethylene glycol monomethylester. After the reaction solution was allowed to stand at ambient temperature for 5 minutes, absorbance (a) at 382 nm of the reaction solution was measured. For the blank test, the above procedure was repeated using said buffer solutions without the test compound, and the absorbance (b) was measured in the blank test. The percentage for inhibition to carboxypeptidase A was calculated according to the equation:

$$\frac{(b-a)}{b} \times 100$$

On the basis of the values of percentages of inhibition measured by the above procedure, 50% Inhibition Concentration (IC$_{50}$) was evaluated. The results are shown in Table 1 below.

TABLE 1

| No. | Test Compounds | IC$_{50}$ (μg/ml) |
|---|---|---|
| 1 | Compound of Example 1 (b) | 0.02 |
| 2 | Compound of Example 2 (b) | 0.0088 |
| 3 | Compound of Example 3 (b) | 0.064 |
| 4 | Compound of Example 4 (b) | 0.35 |

(2) The effect on cell-mediated or cellular immunity:

The effect of the new arphamenine-related compounds on cell-mediated or cellular immunity was evaluated by measuring Delayed Type Hypersensitivity (D.T.H.) using mice which received sheep red blood cell inoculated as antigen into the footpad of mice for immunization (see P. H. Lagrange, G. B. Mackaness and T. E. Miller: "J. Exp. Med.", 139, 1529–1539 (1974)).

Test Procedure:

A suspension of 10$^8$ sheep red blood cells (SRBC) in 0.05 ml of physiological saline was subcutaneously injected into one footpad of each $CDF_1$-mouse (female, 8 weeks-aged, 5 mice in each group) for immunization. Simultaneously, the mouse under test was given orally the test compound at a dosage of 5 mg/Kg, 0.5 mg/Kg or 0.05 mg/Kg as a solution of the test compound which was prepared by dissolving the test compound in physiological saline and then filtering the resulting solution by a millipore filter. On 4 days after the administration of the test compound, $10^8$ sheep red blood cells were subcutaneously injected into another footpad of each test mouse for secondary challenge of the D.T.H. response. 24 Hours after the challenge, the thickness of the footpads was measured with calipers. Concurrently, the thickness of footpad of control mice which had received the injection of SRBC and physiological saline without the administration of the test compound was also measured in each mouse.

The effect of the test compound on the DTH response was evaluated by a percentage of increase in footpad thickness as calculated according to the following equation:

$$\text{Percentage of increase in footpad thickness} = \frac{\text{Mean value } (T) \text{ of the increase in footpad thickness in mice treated with test compound}}{\text{Mean value } (C) \text{ of the increase in footpad thickness in mice untreated}} \times 100$$

The test results are shown in Table 2 below.

TABLE 2

Effect on establishment of D.T.H. response with sheep red blood cells.

| Test Compounds | Dosages (mg/Kg) | Percentage of increase in footpad thickness |
|---|---|---|
| Compound of Example 1 (b) | 5 | 128* |
| | 0.5 | 121 |
| | 0.05 | 107 |
| Compound of Example 2 (b) | 5 | 144* |
| | 0.5 | 130* |
| | 0.05 | 113 |
| Compound of Example 3 (b) | 5 | 136* |
| | 0.5 | 120 |
| | 0.05 | 110 |
| Compound of Example 4 (b) | 5 | 145* |
| | 0.5 | 123* |
| | 0.05 | 110 |

*$P < 0.05$

Toxicity of the compound of the formula (I) was assessed with the compounds of Examples 1, 2, 3 and 4 in the following way: Thus, 100 mg/Kg of the test compound was intraperitoneally administered in ICR-strain mice (male, 5 weeks-aged, weight 20 g), when it was found that no death was caused by the final compounds obtained in the Examples 1 to 4.

From these observations, it is clear that the new arphamenine-related compound of the formula (I) according to this invention enhances the cell-mediated immunity even when given at a low dosage. This strong immunopotentiating activity of the new compounds of this invention shows that these compounds are useful widely in immunotherapeutic treatment of tumors, and also as an agent of preventing bacterial infections.

The arphamenine-related compound according to this invention may be administered as a pharmaceutical composition which comprises the compound of the formula (I) as the active ingredient, in association with a pharmaceutically acceptable known carrier for the active ingredient and which may be in any form of oral preparations, injections and rectal suppositories, when it is used as the immunopotentiating agent. These compositions may be formulated into various forms by admixing the compound (I) with a pharmaceutically acceptable carrier, if desired, together with different kinds of pH adjustors, stabilizers, and excipients. The dosage of the arphamenine-related compound of the formula (I) may vary depending on conditions of the diseases, but a usual dosage of the compound may be 50 to 200 mg in oral administration for adult once a day.

According to a second aspect of this invention, therefore, there is provided a pharmaceutical composition for use as immunopotentiator, which comprises an immunopotentiatingly effective amount of the compound of the formula (I) as defined hereinbefore or a pharmaceutically acceptable salt or ester thereof as the active ingredient, in association with a pharmaceutically acceptable carrier for the active ingredient.

According to a third aspect of this invention, there is provided a method of potentiating the immune response in a living animal, including man, which comprises administering to the animal an immunopotentiatingly effective amount of the compound of the formula (I) as defined hereinbefore or a pharmaceutically acceptable salt or ester thereof.

This invention is now described with reference to the following Examples of this invention, to which this invention is not limited.

EXAMPLE 1

(a) Synthesis of 5-benzoylamino-8-guanidino-4-oxo-2-phenylmethyloctanoic acid

Arphamenine A hydrochloride (200 mg) was dissolved in 1 ml of water, and to the resulting solution were added 98 μl of benzoyl chloride and 119 mg of sodium carbonate, each in 1/5 portions at 30 minutes-interval and totally five times, under ice-cooling and stirring. After the reaction was completed, the reaction mixture was adjusted to pH 7.0 with 1N HCl, followed by addition of ethyl ether thereto. The precipitate as formed was washed with water and dried to give 225 mg of the titled compound as a colorless powder. This product gave a value of m/z 425 (MH+) in mass spectrometry.

Elemental analysis (for $C_{23}H_{28}N_4O_4$, molecular weight 424.5):
Found: C 64.55, H 7.01, N 12.88%,
Calcd.: C 65.08, H 6.65, N 13.20%.

(b) Synthesis of 5-benzoylamino-8-[(4,6-dimethylpyrimidin-2-yl)amino]-4-oxo-2-phenylmethyloctanoic acid

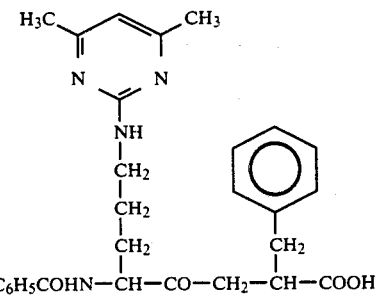

The compound (87 mg) obtained in the above step (a), acetylacetone, namely 2,4-pentanedione (126 mg)

and anhydrous potassium carbonate (100 mg) were dissolved in 1.5 ml of dioxane-water (1:1), followed by stirring the solution at 37° C. overnight to effect the reaction. After the reaction was completed, the reaction mixture was adjusted to pH 5.0 by addition of 1N hydrochloric acid, and concentrated to dryness. The residue obtained was chromatographed in a column of silica-gel (5 g) by eluting with a mixture of chloroform and methanol, while changing the ratio of chloroform to methanol in said mixture gradiently from 50:1 to 20:1. The desired reaction product was eluted out in fraction Nos. 16 to 24 (in chloroform-methanol (20:1)) of the eluate. These fractions were combined together and concentrated to give 54 mg of the titled compound as a colorless powder. This product gave a value of m/z 489 (MH+) in mass spectrometry.

Elemental analysis (for $C_{28}H_{32}N_4O_4$, molecular weight 488.59):
 Found: C 68.66, H 6.77, N 11.27%,
 Calcd.: C 68.83, H 6.60, N 11.47%.

The above titled compound as produced in this Example 1(b) showed a melting point of 134° to 137° C., and its infrared absorption spectrum (pelleted in KBr) is as shown in FIG. 1 of the attached drawings. Nuclear magnetic resonance absorption spectrum ($^1$H-NMR) of the compound of Example 1(b) (in solution in deutero-methanol-deuterochloroform, δppm., 200 MHz) showed absorptions at 1.52–2.03 ($CH_2 \times 2$), 2.21 ($CH_3 \times 2$), 2.39–3.29 (CH, $CH_2 \times 3$), 4.74 (CH), 6.24(CH), 7.1–7.3 ($C_6H_5$), 7.54 ($C_6H_5$).

EXAMPLE 2

(a) Synthesis of 5-benzoylamino-8-guanidino-2-(4'-hydroxyphenylmethyl)-4-oxo-octanoic acid Arphamenine B hydrochloride (300 mg) was dissolved in 2 ml of water, and to the resulting solution were added 140 μl of benzoyl chloride and 170 mg of sodium carbonate, each in 1/5 portions at 30 minutes-intervals and totally five times, under ice-cooling and stirring. After the reaction was completed, the reaction mixture was adjusted to pH 7.0 by addition of 1N hydrochloric acid, followed by addition of ethyl ether thereto. The precipitate as formed was washed with water and dried to give 270 mg of the titled compound as a colorless powder. This product gave a value of m/z 441 (MH+) in mass spectrometry.

Elemental analysis (for $C_{23}H_{28}N_4O_5$, molecular weight 440.5):
 Found: C 62.96, H 6.61, N 12.63%,
 Calcd.: C 62.70, H 6.41, N 12.72%.

(b) Synthesis of 5-benzoylamino-8-[(4,6-dimethylpyrimidin-2-yl)amino]-2-(4'-hydroxyphenylmethyl)-4-oxo-octanoic acid The compound (220 mg) obtained in the above step (a), acetylacetone, namely 2,4-pentanedione (315 mg) and anhydrous potassium carbonate (100 mg) were dissolved in 1.5 ml of dioxane-water (1:1), and the resultant solution was stirred at 37° C. overnight to effect the reaction. After the reaction was completed, the reaction mixture was adjusted to pH 5.0 with 1N hydrochloric acid. The reaction mixture was then concentrated to dryness. The residue obtained was chromatographed in a column of silica gel (5 g) by eluting with a mixture of chloroform and methanol, while changing the ratio of chloroform to methanol in said mixture gradiently from 50:1 to 10:1. The desired reaction product was eluted out in fraction Nos. 22 to 31 [in chloroform-methanol (10:1)] of the eluate. These fractions were combined together and concentrated to dryness to afford 59 mg of the titled compound as a colorless powder. This product gave a value of m/z 505 (MH+) in mass spectrometry.

Elemental analysis (for $C_{28}H_{32}N_4O_5$, molecular weight 504.58):
 Found: C 66.23, H 6.80, N 10.72%,
 Calcd.: C 66.65, H 6.39, N 11.10%.

Figure 2:
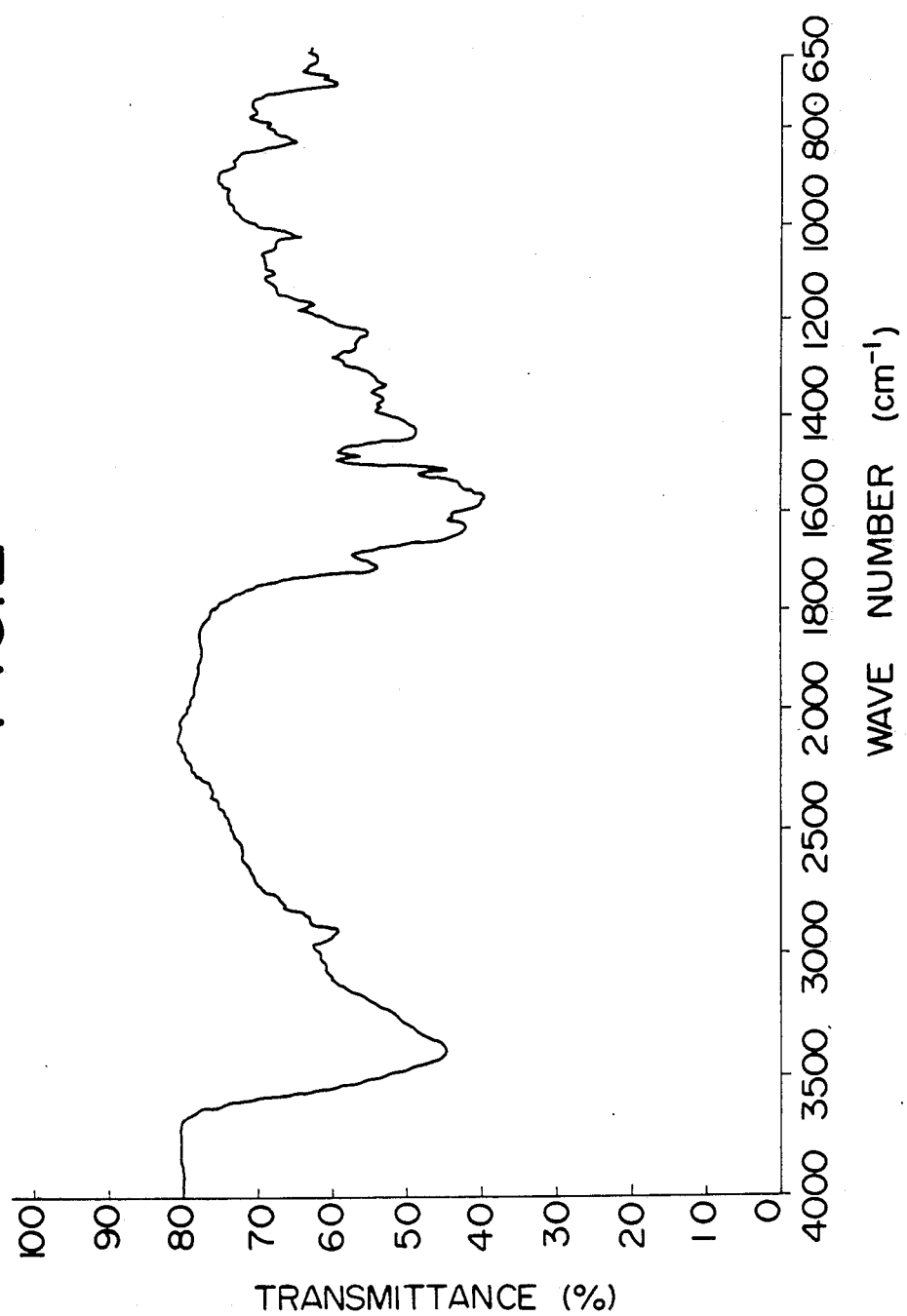

The above titled compound as produced in this Example 2(b) showed a melting point of 110°–113° C., and its infrared absorption spectrum (pelleted in KBr) is as shown in FIG. 2 of the attached drawings. Nuclear magnetic resonance absorption spectrum ($^1$H-NMR) of the compound of Example 2(b) (in solution in deutero-methanol-deutero-chloroform, δppm., 200 MHz) showed absorptions at 1.26–2.19 ($CH_2 \times 2$), 2.29 ($CH_3 \times 2$), 2.29–3.30 (CH, $CH_2 \times 3$), 4.77 (CH), 6.31 (CH), 6.80 ($C_6H_4$), 7.54 ($C_6H_5$).

EXAMPLE 3

(a) Synthesis of 5-benzyloxycarbonylamino-8-guanidino-4-oxo-2-phenylmethyloctanoic acid Arphamenine A hydrochloride (150 mg), sodium hydrogen carbonate (176 mg) and S-benzyloxycarbonyl-4,6-dimethyl-2-mercaptopyrimidine (230 mg) were dissolved in 20 ml of dioxane-water (1:1), and the resultant solution was stirred at room temperature overnight. After the reaction was completed, the reaction solution was adjusted to pH 2.0 with 1N hydrochloric acid, followed by extraction with n-butanol. The extract in n-butanol was washed with water and concentrated to dryness. The residue obtained was chromatographed in a column of silica-gel (20 g) by eluting with a mixture of chloroform and methanol, while changing the ratio of chloroform to methanol in said mixture gradiently from 15:1 to 2:1. The desired reaction product was eluted out in fraction Nos. 60 to 120 [in chloroformmethanol (2:1)] of the eluate. These fractions were combined together and concentrated to dryness to afford 116 mg of the titled compound as a colorless powder. This product gave a value of m/z 455 ($M^H+$) in mass spectrometry.

Elemental analysis (for $C_{24}H_{30}N_4O_5 \cdot H_2O$ weight 472.54):
 Found: C 61.37, H 6.68, N 11.70%,
 Calcd.: C 61.00, H 6.83, N 11.86%.

(b) Synthesis of 5-benzyloxycarbonylamino-8-[(4,6-dimethylpyrimidin-2-yl)amino]-4-oxo-2-phenylmethyloctanoic acid The compound (110 mg) obtained in the step (a) just above, acetylacetone (150 mg) and anhydrous potassium carbonate (100 mg) were dissolved in 1.5 ml of dioxanewater (1:1), and the solution was stirred at 37° C. overnight to effect the reaction. After the reaction was completed, the reaction mixture was adjusted to pH 5.7 with 1N hydrochloric acid and then concentrated to dryness. The residue obtained was chromatographed in a column of silica-gel (5 g) by eluting with a mixture of chloroform and methano, while changing the ratio of chloroform to methanol in said mixture gradiently from 50:1 to 10:1. The desired reaction product was eluted out in fraction Nos. 8 to 70 of the eluate. These fractions were combined together and concentrated to dryness to afford 78 mg of the titled compound as a colorless powder. This product gave a value of m/z 519 (MH+) in mass spectrometry.

Elemental analysis (for $C_{29}H_{34}N_4O_5 \cdot \frac{1}{2}H_2O$, molecular weight 527.62):

Found: C 66.39, H 6.70, N 10.52%,

Calcd.: C 66.02, H 6.69, N 10.62%.

Figure 3:
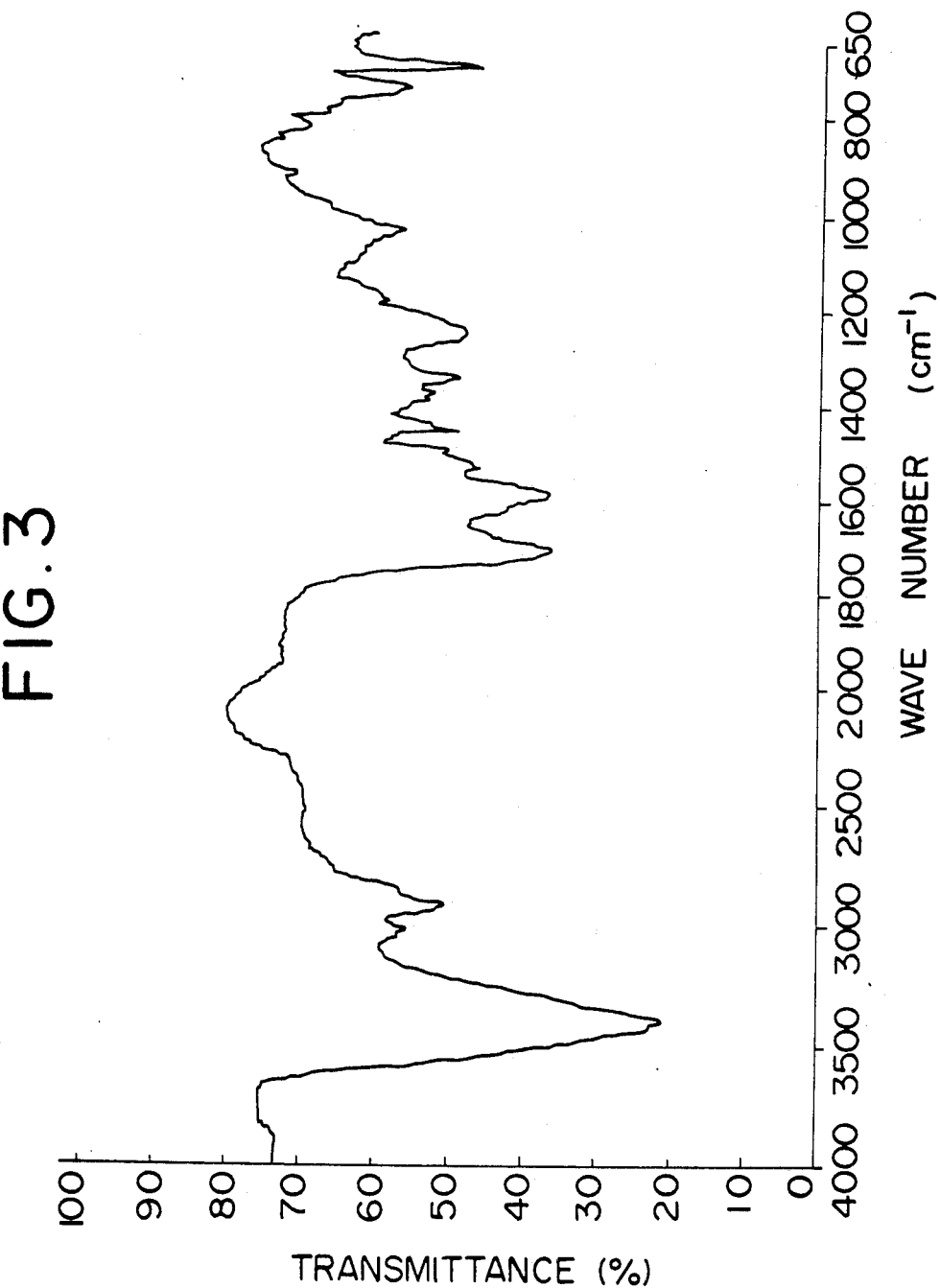

The titled compound as produced in this Example 3(b) exhibited an infrared absorption spectrum (pelleted in KBr) as shown in FIG. 3 of the attached drawings. Nuclear magnetic resonance absorption spectrum ($^1$H-NMR) of the compound of Example 3(b) (in solution in deutero-chloroform, δppm., 200 MHz) showed absorptions at 1.48–2.00 (CH$_2$×2), 2.23 (CH$_3$×2), 2.45–3.45 (CH, CH$_2$×3), 4.26 (CH), 5.00 (CH$_2$), 6.16 (CH), 7.05–7.27 (C$_6$H$_5$×2).

EXAMPLE 4

(a) Synthesis of 5-benzyloxycarbonylamino-8-guanidino-2-(4′-hydroxyphenylmethyl)-4-oxooctanoic acid Arphamenine B hydrochloride (150 mg), sodium hydrogen carbonate (176 mg) and S-benzyloxycarbonyl-4,6-dimethyl-2-mercapto-pyrimidine (230 mg) were dissolved in 20 ml of dioxane-water (1:1), and the solution was stirred at room temperature overnight. After the reaction was completed, the reaction solution was adjusted to pH 2.0 with 1N hydrochloric acid, followed by extraction with n-butanol. The extract in n-butanol was washed with water and then concentrated to dryness. The residue obtained was dissolved in water containing 40% methanol, and the resulting solution was passed through a column of CM-Sephadex C-25 (H$^+$, 15 ml). The column was washed with 40% methanol-water and then eluted with water containing 40% methanol and 0.01N hydrochloric acid. The desired reaction product was eluted out in fraction Nos. 8 to 20 of the eluate. These fractions were combined together and adjusted to pH 2.0, and again extracted with n-butanol. The extract in n-butanol obtained was washed with water and then concentrated to dryness to obtain 167 mg of the titled compound as a colorless powder. This product gave a value of m/z 471 (MH$^+$) in mass spectrometry.

Elemental analysis (for C$_{24}$H$_{30}$N$_4$O$_6$·½H$_2$O, molecular weight 479.53):

Found: C 60.41, H 6.55, N 11.51%,

Calcd.: C 60.11, H 6.52, N 11.68%.

(b) Synthesis of 5-benzyloxycarbonylamino-8-[(4,6-dimethylpyrimidin-2-yl)amino]-2-(4′-hydroxyphenylmethyl)-4-oxo-octanoic acid The compound (150 mg) obtained in the step (a) just above, acetylacetone (200 mg) and anhydrous potassium carbonate (100 mg) were dissolved in 1.5 ml of dioxane-water (1:1), and the solution was stirred at 37° C. overnight to effect the reaction. After the reaction was completed, the reaction solution was adjusted to pH 5.7 with 1N hydrochloric acid and concentrated to dryness. The residue obtained was dissolved in methanol and the resultant solution was filtered to remove the methanol-insoluble matters therefrom. The solution as filtered was chromatographed in a column of silica-gel (5 g) by eluting with a mixture of chloroform and methanol, while changing the ratio of chloroform to methanol in said mixture gradiently from 50:1 to 10:1. The desired reaction product was eluted out in fraction Nos. 13 to 41 of the eluate. These fractions were combined together and concentrated to dryness to afford 109 mg of the titled compound as a colorless powder. This product compound gave a value of m/z 544 (MH$^+$) in mass spectrometry.

Elemental analysis (for C$_{29}$H$_{34}$N$_4$O$_6$·½H$_2$O, molecular weight 543.62):

Found: C 64.13, H 6.26, N 9.96%,

Calcd.: C 64.07, H 6.49, N 10.31%.

Figure 4:
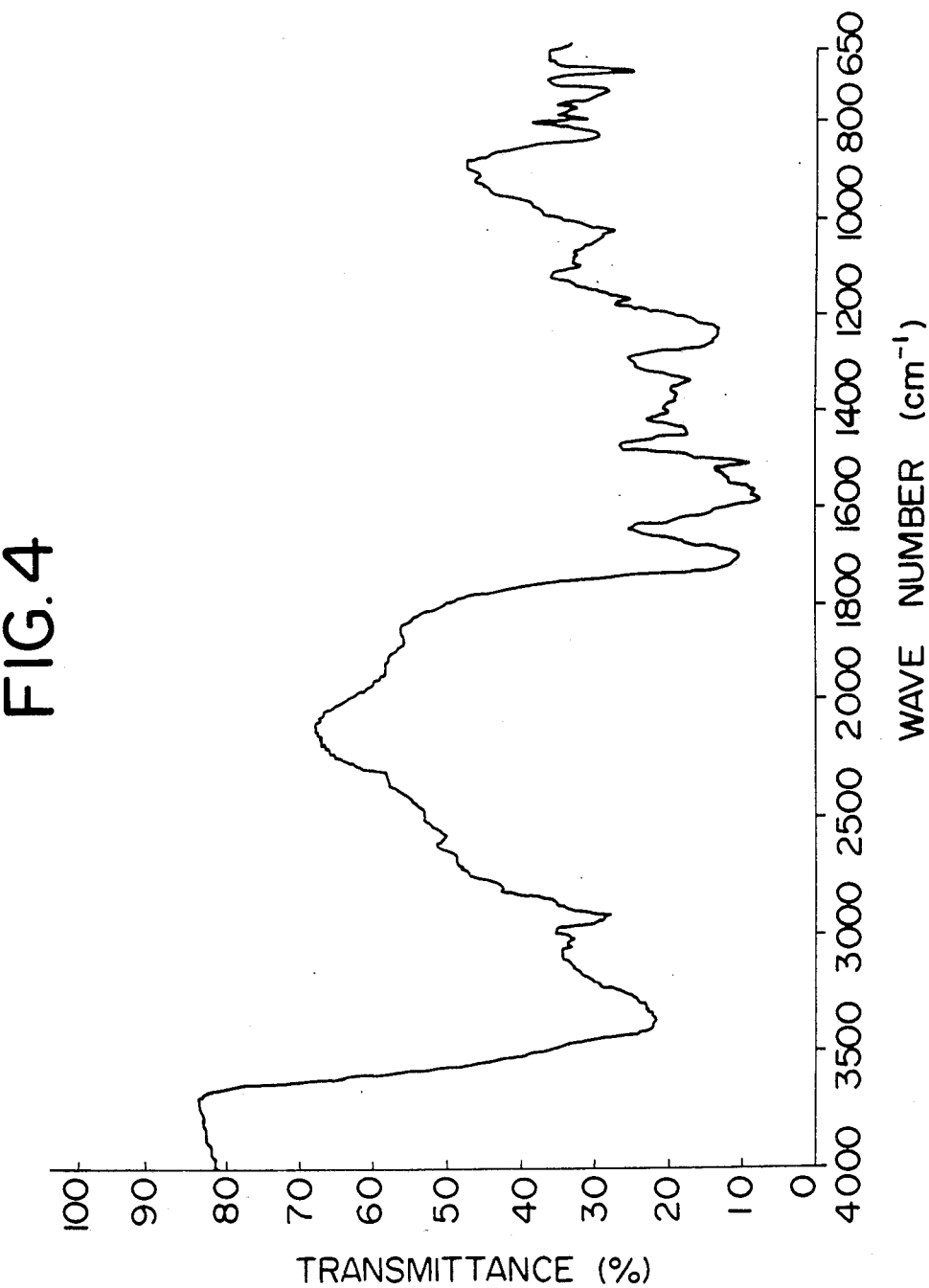

The titled compound as produced in this Example 4(b) showed a melting point of 100°–103° C., and its infrared absorption spectrum (pelleted in KBr) is as shown in FIG. 4 of the attached drawings. Nuclear magnetic resonance absorption spectrum ($^1$H-NMR) of the compound of Example 4(b) (in solution in deutero chloroform, δppm., 200 MHz) showed absorptions at 1.47–1.98 (CH$_2$×2), 2.26 (CH$_3$×2), 2.35–3.44 (CH, CH$_2$×3), 4.14 (CH), 5.06 (CH$_2$), 6.35 (CH), 6.83 (C$_6$H$_4$). 7.26–7.38 (C$_6$H$_5$).

What we claim is:

1. An arphamenine-related compound represented by the formula:

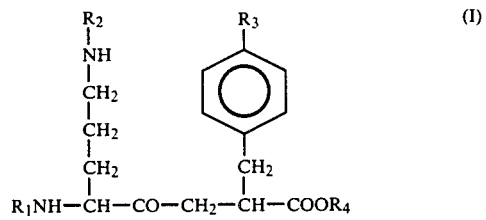

wherein R$_1$ denotes a hydrogen atom, an alkoxycarbonyl group, an aralkoxy-carbonyl group, or an acyl group, R$_2$ denotes a dimethylpyrimidinyl group, R$_3$ denotes a hydrogen atom or a hydroxyl group, and R$_4$ denotes a hydrogen atom, an alkyl group, or an aralkyl group, or a pharmaceutically acceptable salt or ester thereof.

2. A compound as claimed in claim 1, in which R$_1$ is a hydrogen atom, a benzoyl group or a benzyloxycarbonyl group, R$_2$ is a 4,6-dimethylpyrimidin-2-yl group, R$_3$ is a hydrogen atom or a hydroxyl group, and R$_4$ is a hydrogen atom in the formula (I) as defined in claim 1.

3. A compound as claimed in claim 1 which is selected from:- 5-benzoylamino-8-[(4,6-dimethylpyrimidin-2-yl) amino]-4-oxo-2-phenylmethyl-octanoic acid; 5-benzoylamino-8-[(4,6-dimethylpyrimidin-2-yl)amino]-2-(4′-hydroxyphenylmethyl)-4-oxo-octanoic acid., 5-benzyloxycarbonylamino-8-[(4,6-dimethylpyrimidin-2-yl)amino]-4-oxo-2-phenylmethyloctanoic acid; and 5-benzyloxycarbonylamino-8-[(4,6-dimethylpyrimidin-2-yl)amino]-2-(4′-hydroxyphenylmethyl)-4-oxo-octanoic acid.

4. A pharmaceutical, immunopotentiating composition comprising an immunopotentiatingly effective amount of a compound of the formula (I) as defined in claim 1 or a pharmaceutically acceptable salt or ester thereof as the active ingredient, in association with a pharmaceutically acceptable carrier for the active ingredient.

5. A method of potentiating the immune response in a living animal, including man, which comprises administering to the animal an immunopotentiatingly effective amount of a compound of the formula (I) as defined in claim 1 or a pharmaceutically acceptable salt or ester thereof.

* * * * *